United States Patent [19]

Lai et al.

[11] Patent Number: 5,384,315

[45] Date of Patent: Jan. 24, 1995

[54] THIOPHENE SUBSTITUTED CYCLOAMINES, COMPOSITIONS AND USE

[75] Inventors: Kiong H. Lai, Guelph; Wan S. Yu, Toronto, both of Canada; Robert A. Davis, Cheshire, Conn.

[73] Assignees: Uniroyal Chemical Company, Inc., Middlebury, Conn.; Uniroyal Chemical Ltd./Ltee, Elmira, Canada

[21] Appl. No.: 195,308

[22] Filed: Feb. 14, 1994

[51] Int. Cl.⁶ .................... A01N 43/40; A01N 43/84; C07D 409/06; C07D 413/06

[52] U.S. Cl. .................... 514/231.5; 514/307; 514/314; 514/326; 514/422; 544/146; 546/148; 546/165; 546/212; 548/468

[58] Field of Search .............. 544/146; 546/148, 165, 546/212; 548/468; 514/231.5

[56] References Cited

U.S. PATENT DOCUMENTS 2,526,319  10/1950  Beatty III .................... 546/212
4,202,894   5/1980  Pfiffner.
4,950,671   8/1990  Lai et al.

OTHER PUBLICATIONS

J. Org. Chem., pp. 3820–3821, vol. 36, No. 24, entitled Side-Chain Amination during the Reaction of Methylbromothiophenes with Potassium Amide, by M. G. Reinecke, H. W. Adickes and C. Pyun, published 1971. Agricultural Chemicals, Book IV—Fungicides, Thomson Publications, 1991 Revision, by W. T. Thomson, pp. 142–143.

*Primary Examiner*—Robert W. Ramsuer
*Attorney, Agent, or Firm*—Jerome D. Drabiak

[57] ABSTRACT

A class of compounds having the structural formula

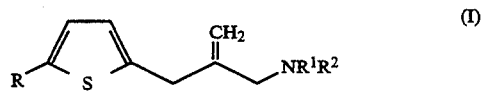

in which R is $C_1$–$C_8$ alkyl, $C_3$–$C_6$ cycloalkyl, phenyl or substituted phenyl; N, $R^1$ and $R^2$ form a monocyclic or bicyclic nitrogen heterocycle which is at least partially saturated and which may contain oxygen or sulfur or be substituted with lower alkyl; and physiologically acceptable salts thereof is disclosed.

A process for forming the thiophene substituted cycloamines of the subject invention is described. A composition comprising the compound of the subject invention and a suitable carrier therefor is taught.

A method of controlling phytopathogenetic fungi is disclosed. In this method a fungicidally effective amount of the compound of the present invention is applied to the locus to be protected.

11 Claims, No Drawings

THIOPHENE SUBSTITUTED CYCLOAMINES, COMPOSITIONS AND USE

TECHNICAL FIELD

Our invention, in general, is directed to a new class of thiophene substituted cycloamines. Our present invention, stated more particularly, is directed to a new class of thiophene substituted cycloamines which we have found to be useful as fungicides.

BACKGROUND ART

The control of phytopathogenetic fungi is of significant economic importance. Fungal growth on plants and plant portions—notably stems, blossoms, foliage and root systems—is known to inhibit growth of plants and to undesirably affect production of commercially valuable crops such as fruits, vegetables and seeds.

The use of nitrogen-containing heterocyclic compounds to provide fungicidally effective compositions is known in the art.

In particular, U.S. Pat. No. 4,202,894 to Pfiffner discloses a select class of heterocyclic compounds—principally morpholines and piperidines—which are said to be useful as fungicidal agents.

Additionally, 4-(3-(4-(1,1-dimethylethyl) phenyl)-2-methyl) propyl-2,6-(cis)-dimethylmorpholine—a compound that is said to possess activity as a systemic, foliar fungicide—is disclosed in *Agricultural Chemicals, Book IV—Fungicides*, 1991 Revision, by W. T. Thomson, Thomson Publications, P.O. Box 9335, Fresno, Calif. 93791 at page 142.

Those skilled in the art know there is an ongoing, continual need to develop new compounds that provide ever more effective fungicidai activity against the scourge of phytopathogenetic fungi.

While organic compounds of the above-mentioned prior art may be generally classified as nitrogen-containing heterocyclic compounds, those skilled in the art know that the sorts of heterocyclic compounds as are disclosed in the above-mentioned prior art, are characterized by structure which is markedly distinguishable from a substituted 2-propenyl derivative of a nitrogen-containing heterocyclic compound.

For example, U.S. Pat. No. 4,950,671 to Lai and Davis (two of us) discloses substituted 2-propenyl derivatives of pyridine, which include a substituted benzene ring. Those skilled in the art are well aware that such structure is clearly distinguishable from a substituted thiophene.

In particular, various substituents have been synthesized onto the thiophene ring of our present invention, thus making our new compounds structurally unique and distinguishable from the prior art.

It is, of course, imperative that any new fungicides that come onto the market and which possess desired fungicidal activity not possess any undesirable activity.

SUMMARY DISCLOSURE OF INVENTION

A new class of thiophene substituted cycloamines has been discovered. Our new class of thiophene substituted cycloamines provides effective control of many commonly-encountered phytopathogenetic fungi. Moreover, not only is our new class of compounds surprisingly effective against many common fungi but, in addition, our new class of compounds can effectively be used to control fungi by either systemic or foliar treatment.

In accordance with our present invention, we are pleased to disclose a new class of compounds having the structural formula I

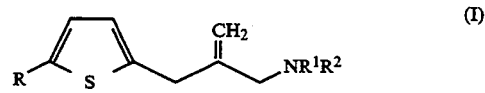

wherein R is $C_1$–$C_8$ alkyl, $C_3$–$C_6$ cycloalkyl, phenyl, substituted phenyl, phenylalkyl, substituted phenylalkyl, phenoxyalkyl, substituted phenoxyalkyl, aromatic heterocycle, or substituted aromatic heterocycle; wherein N, $R^1$ and $R^2$ form a monocyclic or bicyclic nitrogen heterocycle which is at least partially saturated and which may contain oxygen or sulfur or be substituted with lower alkyl. Further, the full scope of our invention includes all physiologically acceptable salts of our above-recited new class of compounds.

Further in accordance with our present invention there is herein disclosed a method or process for forming the thiophene substituted cycloamines of our invention. In one illustrative embodiment of our method or process, a thiophene substituted 2-propenyl halide of the structure II

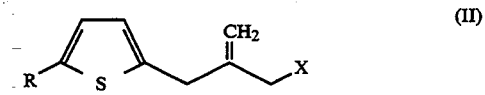

is heated with a cycloamine of the structure III

where X, a leaving group, represents a halogen atom.

Also disclosed herein and within the scope of our present invention is a composition-of-matter which comprises our above-recited new class of compounds in combination with a suitable carrier therefor.

Yet another aspect of our present invention is directed to a method of controlling fungi. In one such illustrative method that is disclosed herein, a fungicidally effective amount of our above-recited new class of compounds is applied to a particular locus that is to be protected.

Other aspects, features and advantages of our present invention are discussed in greater detail hereinbelow.

DETAILED DESCRIPTION OF INVENTION

The compound of our present invention is a thiophene substituted cycloamine having the structural formula I

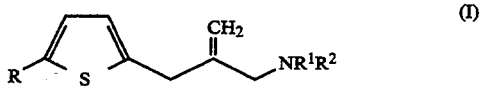

wherein R is $C_1$–$C_8$ alkyl, $C_3$–$C_6$ cycloalkyl, phenyl or substituted phenyl, phenylalkyl or substituted phenylalkyl, phenoxyalkyl or substituted phenoxyalkyl, aromatic heterocycle or substituted aromatic heterocycle; wherein N, $R^1$ and $R^2$ form a monocyclic or bicyclic nitrogen heterocycle which is at least partially saturated and which may contain oxygen or sulfur or be substituted with lower alkyl; and physiologically acceptable salts thereof.

Preferably, the novel compound of our present invention has the structural formula I disclosed above, wherein R is $C_4$ to $C_8$ alkyl, phenyl, or phenylmethyl; and physiologically acceptable salts thereof.

More preferably, the novel compound of our present invention has the structural formula I disclosed above, wherein R is 1,1-dimethylethyl, 1,1-dimethylpropyl, 5-phenylmethyl, 3-methylbutyl, or 3,3-dimethylbutyl; wherein N, $R^1$ and $R^2$ form isoquinolinyl-, partially saturated isoquinolinyl-, piperidinyl-, morpholinyl-, or quinolinyl- which may be substituted with $C_1$-$C_2$ alkyl; and physiologically acceptable salts thereof.

In a particularly preferred embodiment of the novel compound of our present invention, where the above-discussed nitrogen heterocycle that is formed of N, $R^1$ and $R^2$ is substituted with lower alkyl groups, the number of such alkyl substituents is preferably 1 or 2.

In still another particularly preferred embodiment of our present invention, where our above-recited structural formula I is utilized, a physiologically acceptable salt is preferably a hydrochloride salt.

In accordance with yet another aspect of our present invention, a method or process for making the above-discussed compounds having the structural formula I is provided. In one such illustrative process, a thiophene substituted 2-propenyl halide of the structure II

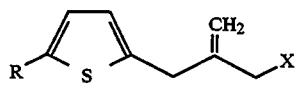 (II)

is heated with a cycloamine of the structure III $HNR^1R^2$ (III)

where X, a leaving group, represents a halogen atom. Illustrative halogen atoms include chlorine, bromine and iodine.

Thus, a thiophene substituted 2-propenyl halide of structure II and a cycloamine of structure III may be heated together, preferably in the absence of solvent, to a temperature between 80° C. and 130° C. If a solvent is used, the reactants represented by the structures II and III may be heated together to the reflux temperature of the solvent.

Preferred solvents include inert hydrocarbons and halogenated hydrocarbons. Illustrative particularly preferred solvents include toluene, xylene and dichlorobenzene.

Compounds with the structures of formula I may be obtained by reacting two molar equivalents of cycloamine of structure III with one molar equivalent of the halide of structure II. The resulting crude product may advantageously be neutralized with base prior to the isolation of the product represented by structure I.

Compounds of structure I typically form acid addition salts with organic and inorganic acids. Acid addition salts of these sorts are within the scope of our present invention. Such salts can readily be obtained by customary methods familiar to those skilled in the art.

For example, a compound of structure I may advantageously be dissolved in a suitable inert solvent; and a mineral acid, such as hydrochloric acid, may then be added to the solvent.

When hydrochloric acid is thus utilized, the resulting salt that forms is the hydrochloride salt of the compound described by formula I. Other mineral acids which may advantageously be used in forming a salt that is within the contemplation of our present invention include nitric and sulfuric acids.

The resulting salt thus formed may then advantageously be isolated in a known manner such as by simple filtration; or, if further purification is deemed necessary, by washing with an inert organic solvent.

It can be appreciated and should be noted, in the case where N, $R^1$ and $R^2$ form a monocyclic nitrogen ring that is substituted with two or more lower alkyl groups, that a compound of formula I may be present as more than one stereoisomer, as is depicted by the structure A below where $R^3$, $R^4$, $R^5$ and $R^6$ are hydrogen or lower alkyl and Z is oxygen, sulfur, or methylene.

In particular, if two or more of these "R" groups are alkyl, cis and trans isomers are possible. Isomers of these sorts, which may or may not be separable, are within the scope of our invention.

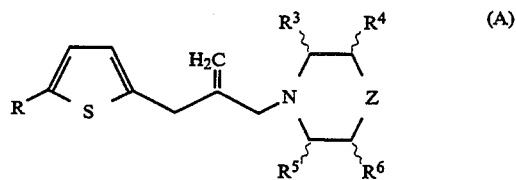 (A)

It should be further noted, in the case where N, $R^1$ and $R^2$ form a bicyclic nitrogen ring, that the compound of formula I may be present as a pair of cis and trans isomers. Such cis and trans isomers, which may or may not be separable, are also within the scope of this invention.

The intermediate 2-propenyl halide of structure II may be prepared by reaction of an appropriate Grignard reagent with methallyl dihalide, as is shown below in equations IV and V. Preferably, the halogen of the methallyl dihalide moiety is either bromine or chlorine. More preferably, the halogen is chlorine. Our preferred solvent for this Grignard reaction is either diethyl ether or tetrahydrofuran. A variety of thiophene-substituted 2-propenyl halides were prepared. The following examples illustrate the preparation of certain of these compounds and are summarized in Table I.

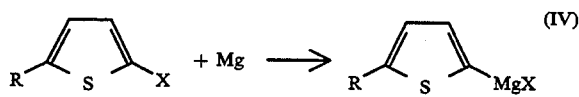 (IV)

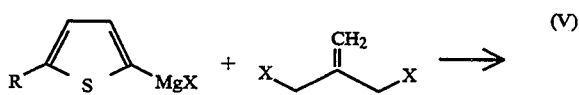 (V)

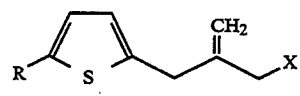

The 2-thienyl halide structure depicted above can be prepared via procedures, known in the literature, as are published in *J. Org. Chem.*, Vol.36, No.24, pp.3820–3821 (1971). Also, 2-substituted thiophenes of the structure VI

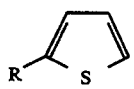

(VI)

are widely known in the literature and may be prepared by a variety of methods familiar to those skilled in the art. Included among these known methods are the Grignard method, similar to that shown above, wherein a 2-halothiophene is reacted with magnesium and the resulting Grignard reagent is then reacted with a haloalkane.

Another example of a known method of synthesis of 2-substituted thiophenes is Friedel-Crafts acylation in which thiophene is acylated with an acid chloride and the resulting thiophene ketone is then reduced by Clemmensen reduction or Wolff-Kishner reduction to give the desired 2-substituted thiophene. Required reagents for these reactions are readily available commercially and are widely reported throughout the literature.

Yet another aspect of our present invention is directed to a process or method for controlling phytopathogenetic fungi.

In one such illustrative method of our invention, a fungicidally effective amount of the compound of structure I is applied to the locus under attack by certain fungi, the control of which is desired.

Our preferred method of controlling particular phytopathogenetic fungi comprises applying a fungicidally effective amount of a compound having the structural formula I to the locus under attack by such fungi. Moreover, in such a compound having the structural formula I, the R and $R^1$ moieties have specifically been selected, and the compound screened and tested, so as to provide the structure I compound with fungicidal activity that is most effective against the targeted fungi.

More preferably, our method of controlling phytopathogenetic fungi comprises applying, to the locus under attack by said fungi, a fungicidally effective amount of a compound having the structural formula I, wherein the R moiety is 1,1-dimethylethyl, 1,1-dimethylpropyl, 5-phenylmethyl, 3-methylbutyl, or 3,3-dimethylbutyl; and wherein N, $R^1$ and $R^2$ form isoquinolinyl-, partially saturated isoquinolinyl-, piperidinyl-, morpholinyl-, or quinolinyl-, which may be substituted with $C_1$–$C_2$ alkyl.

One particularly preferred method comprises applying such a structure I compound to the foliage of the plants to be protected.

Such application, generally called "foliar treatment," is brought about by applying an inert liquid containing the compound of formula I to targeted foliage, at a concentration of between about 10 milligrams to about 500 milligrams of such compound per liter of such inert liquid.

In yet another preferred embodiment of our method of controlling phytopathogenetic fungi, a fungicidally effective amount of the compound of formula I is applied to soil in which plants that are to be protected from targeted fungi are grown. Utilizing this method of application, generally called "systemic treatment," the compound of formula I is applied directly to the soil, at a concentration of between about 0.125 kilograms and about 10 kilograms of such compound per hectare (kg/ha) of soil.

Such systemic control more preferably contemplates application of between 0.125 kg/ha and 5 kg/ha of the compound of formula I directly to the soil, to protect the targeted plant.

Regardless of the method used to control fungi, foliar or systemic, application of the compound of formula I may be made either prior to or after infection of the targeted plant by particular fungi.

Moreover, it can well be appreciated by those skilled in the art that the exact dosage, applied systemically or to the foliage, is dictated by the fungus to be controlled and the particular plant to be protected.

In yet another method for controlling phytopathogenetic fungi, the compound of formula I is applied as a coating to seeds of a plant that is to be protected. Such a method provides many of the benefits of the two application embodiments discussed above, namely foliar treatment and systemic treatment. In particular, such fungicidally-active seed coating, containing the compound of formula I, not only protects a targeted plant from fungal infection but also is taken up by the plant systemically, thereby additionally protecting the plant from fungal attack.

In this so-called "seed coating method" of application, we have found that an effective concentration of the compound of formula I, for the above-discussed purposes, is in the range of between about 5 grams and about 75 grams of the compound per hundred kilograms of seed.

Industrial Applicability

Accordingly, one particularly important aspect of our present invention resides in its utility as a fungicide.

Such a fungicidal composition comprises a compound of formula I and a carrier therefor.

A preferred fungicidal composition comprises the compound of formula I, wherein the R moiety is $C_4$ to $C_8$ alkyl, phenyl, or phenyl methyl; and a carrier therefor.

A more preferred fungicidal composition comprises the compound of formula I, wherein the R moiety is 1,1-dimethylethyl, 1,1-dimethyl propyl, 5-phenylmethyl, 3-methylbutyl, or 3,3-dimethylbutyl; wherein N, $R^1$ and $R^2$ form isoquinolinyl-, partially saturated isoquinolinyl-, piperidinyl-, morpholinyl-, or quinolinyl-, which may be substituted with $C_1$–$C_2$ alkyl; and a carrier therefor.

The concentration or amount of compound of formula I that is contained within such a fungicidal composition is effective for providing the fungicidal composition with desired fungicidal activity.

As was mentioned above, the fungicidal composition of our present invention includes a suitable carrier.

Suitable carriers for admixture with the compound of formula I include such solids as finely divided particulate solids, granules, pellets, wettable powders, soluble powders, and the like.

Additional solid carriers that are within the contemplation of our present invention are such organic and inorganic materials as attapulgite clay, sand, vermiculite, corncob, activated carbon, and mineral silicates.

Among the mineral silicates preferred for use in the composition of our present invention are mica, talc, pyrophyllite clays, and the like.

Fungicidal compositions which include the compound of formula I may advantageously be prepared from a solid carrier, such as one of those described immediately above.

One preferred method of preparing such a fungicidal composition is by impregnating the compound of formula I onto the solid carrier.

An alternative preferred method of preparing such a fungicidal composition is by grinding the compound of formula I into a fine powder and then mixing the fine powder with a desired solid carrier into which a surface-active dispersing agent has been added. The resultant wettable powder, containing the compound of formula I in a finely-divided form, can then be dispersed in water and applied as a dispersion.

Such a fungicidally-active dispersion, generally characterized as a liquid composition, can be a liquid solution or emulsion.

A liquid solution is formed by dissolving the compound of formula I in an aqueous or organic solvent. In most cases, the solvent which acts as the carrier, is an organic solvent.

Preferred solvents include aromatic hydrocarbons such as toluene and xylene. Additional solvents that are preferred include such organic compounds as acetone, methanol, isopropanol, tert-butyl alcohol, cyclohexanone, dioxane, dimethylformamide, dimethyl sulfoxide, ethylene dichloride, diacetone alcohol and N-methylpyrrolidone.

A water-containing or aqueous emulsion, another preferred embodiment of a liquid composition within the contemplation of our present invention, is prepared from a solution, as described above, into which a surface active agent has been added.

Surface active agents suitable for purposes of forming effective fungicidal aqueous emulsions within the contemplation of our invention are known to those skilled in the art.

In yet another embodiment of our present invention, our fungicidal composition can take the form of an aerosol. In preparing this aerosol, we prefer to dissolve the compound of formula I in a first solvent.

The first solvent is conventional in the sense that it is not highly volatile. The resulting solution is then admixed with a second solvent that is highly volatile. The volatile second solvent is commonly called a "liquid aerosol carrier."

The aerosol carrier is liquid only under elevated pressure. At ambient temperature and pressure, namely 25 degrees Celsius and one (1) atmosphere pressure, such an aerosol carrier is typically a gas.

Such an aerosol carrier may possess activity other than fungicidal. For example, the carrier may be an insecticide, a herbicide, a bactericide, a nematocide, or may possess other activity.

EXAMPLES

The following examples are set forth to illustrate more clearly, to those skilled in the art, the principles and practice of our invention. It is our intent, moreover, that such examples not limit our invention, but rather be illustrative of the utility of our preferred embodiments.

Example 1

Preparation of
2-[(2-chloromethyl)-2-propenyl]-5-(1,1-dimethylethyl)-thiophene

This example illustrates the preparation of that sort of a 2-propenyl halide of structure II as is presented in Table I, below.

A solution of 2-bromo-5-(tert-butyl)thiophene (19 g) in dry diethyl ether (50 ml) was added dropwise under nitrogen atmosphere into a mixture consisting of magnesium turnings (2.1 g), an iodine crystal and dry ether (100 ml). The resultant reaction mixture was next refluxed for 2 hours, then cooled and transferred to a dropping funnel, and thereafter added dropwise at 10° C. to a mixture consisting of methallyl dichloride (12 g), dichloro(1,3-bis(diphenylphosphino)propane Nickel (II) (0.2 g), and dry ether (100 ml). After complete addition, the resultant mixture was refluxed for 2 hours, then cooled and diluted with 10% HCl. The mixture subsequently was extracted with ether, dried over sodium sulfate and worked up to give a liquid.

The resultant liquid was distilled, providing 13 g of desired product having a boiling point of 97° C. to 106° C. at a pressure of 0.3 mm Hg.

In an analogous manner, thiophene-substituted 2-propenyl halides of structure VII, summarized below in Table I, were prepared.

THIOPHENE-SUBSTITUTED 2-PROPENYL HALIDES

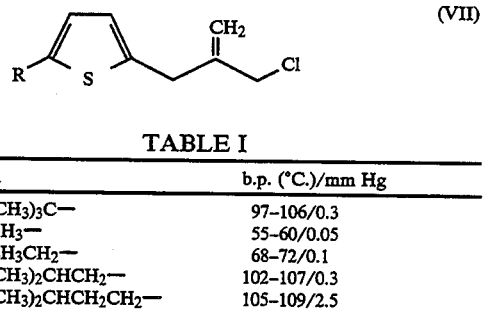

(VII)

TABLE I

| R | b.p. (°C.)/mm Hg |
|---|---|
| $(CH_3)_3C-$ | 97–106/0.3 |
| $CH_3-$ | 55–60/0.05 |
| $CH_3CH_2-$ | 68–72/0.1 |
| $(CH_3)_2CHCH_2-$ | 102–107/0.3 |
| $(CH_3)_2CHCH_2CH_2-$ | 105–109/2.5 |
| ▷−$CH_2-$ | 95–102/0.3 |
| $CH_3CH_2C(CH_3)_2-$ | 120–125/0.2 |
| $C_6H_5-$ | 155–165/0.1 |
| $C_6H_5CH_2-$ | 158–165/0.2 |

Example 2

Preparation Of (Compound Number 6)
4-[2-[[5-(1,1-dimethylethyl)-2-thienyl]methyl]-2-propenyl]-2,6-dimethylmorpholine 2-[[2-(chloromethyl)-2-propenyl]-5-(1,1-dimethylethyl)]thiophene (3 g) and 2,6-dimethylmorpholine (3 g) were combined and together heated at 110° C. for 5 hours, then cooled to room temperature (25° C.), and subsequently treated with 20 ml of 25% sodium hydroxide, to produce a mixture. The resultant mixture was extracted with toluene, dried over sodium sulfate, and subsequently evaporated to give an oil. The resultant oil was distilled to give 3.5 g of Compound Number 6, having a boiling point of 138° C. at 0.3 mm Hg.

Example 3

Preparation Of (Compound Number 3)
4-[2-[[5-(1,1-dimethylethyl)-2-thienyl]methyl]-2-propenyl]-2,6-dimethylmorpholine, hydrochloride A solution consisting of Compound Number 6 (1.4 g) in diethyl ether (50 ml) was treated with a steady stream of hydrogen chloride gas until solid precipitation ceased. The precipitated solid was collected by filtration, washed with ether, and air dried to give 1.2 g of Compound Number 3, having a melting point of 146°–147° C.

Example 4

Preparation Of (Compound Number 13)

1-[2-[[5-(1,1-dimethylethyl)-2-thienyl]methyl]-2-propenyl]-3,5-dimethylpiperidine Analogous to what was described above in Example 2, reaction of 2-[[(2-chloromethyl)-2-propenyl]-5-(1,1-dimethylethyl)]thiophene (3 g) and 3,5-dimethylpiperidine (3 g) at 120° C. provided 3.5 g of Compound Number 13, having a boiling point of 135°–140° C. at 0.3 mm Hg.

Example 5

Preparation Of (Compound Number 10)

1-[2-[[5-(1,1-dimethylethyl)-2-thienyl]methyl]-2-propenyl]octahydro(1H)indole

In another manner analogous to what was described in Example 2, 2-[[(2-chloromethyl)-2-propenyl]-5-(1,1-dimethylethyl)]thiophene (3 g) and perhydroindole (3.3 g) were reacted together at 110° C. for 4 hours to yield 2.5 g of Compound Number 10, having a b.p. of 158°–160° C. at 0.25 mm Hg.

Example 6

Preparation Of (Compound Number 63)

trans-2-[2-[[5-(1,1-dimethylethyl)-2-thienyl]methyl]-2-propenyl]decahydroisoquinoline A mixture consisting of (+) trans-perhydroisoquinoline (9.3 g) and 2-[[2-(chloromethyl)-2-propenyl]-5-(1,1-dimethylethyl)]thiophene (7.5 g) were heated together at 120° C. for 3 hours and subsequently worked up, as described in Example 2, to yield 8.5 g of Compound Number 63 having a boiling point of 160°–164° C. at 0.25 mm Hg.

Example 7

Preparation of Compound Nos. 1, 2, 4, 5, 7–9, 11, 12, 14–62 and 64

Additional compounds of formula I were prepared in accordance with procedures detailed above in Examples 1 through 6. Such additional compounds—as chacterized by their boiling points, melting points, and/or NMR data—are summarized below in Table II. For convenience, these characterizing data for Compounds Nos. 3, 6, 10, 13, and 63, whose syntheses are described above, are included in Table II.

TABLE II

| CMPD NO. | R | $NR^1R^2$ | SALT | b.p. (°C.)/mmHg | m.p. (°C.) |
| --- | --- | --- | --- | --- | --- |
| 1 | —CH$_3$ | (decahydroisoquinoline) | — | 145–148/0.15 | |
| 2 | —CH$_3$ | (octahydroindole) | — | 135–142/0.2 | |
| 3 | (CH$_3$)$_3$C— | (2,6-dimethylmorpholine) | HCl | | 146–147 |
| 4 | —CH$_3$ | (decahydroisoquinoline) | HCl | | 120–121 |
| 5 | (CH$_3$)$_3$C— | (trans-decahydroquinoline) | HCl | | 168–170 |
| 6 | (CH$_3$)$_3$C— | (2,6-dimethylmorpholine) | — | 138/0.3 | |

TABLE II-continued

| CMPD NO. | R | NR¹R² | SALT | b.p. (°C.)/mmHg | m.p. (°C.) |
|---|---|---|---|---|---|
| 7 | $(CH_3)_3C-$ | (trans/cis-decahydroisoquinoline, N-methyl) | — | 167–172/0.3 | |
| 8 | $(CH_3)_3C-$ | (piperidine) | — | 124–126/0.25 | |
| 9 | $(CH_3)_3C-$ | (2,6-dimethylpiperidine) | — | 138–142/0.25 | |
| 10 | $(CH_3)_3C-$ | (octahydroindole) | — | 158–160/0.25 | |
| 11 | $(CH_3)_3C-$ | (3-methylpiperidine) | — | 132/0.3 | |
| 12 | $(CH_3)_3C-$ | (4-methylpiperidine) | — | 132/0.3 | |
| 13 | $(CH_3)_3C-$ | (3,5-dimethylpiperidine) | — | 135–140/0.3 | |
| 14 | $(CH_3)_3C-$ | (2-methylpiperidine) | — | 127–130/0.25 | |
| 15 | $(CH_3)_3C-$ | (1,2,3,4-tetrahydroisoquinoline) | — | 174–178/0.25 | |
| 16 | $(CH_3)_3C-$ | (1,2,3,4-tetrahydroquinoline) | — | 182/0.2 | |

TABLE II-continued
| CMPD NO. | R | NR¹R² | SALT | b.p. (°C.)/mmHg | m.p. (°C.) |
|---|---|---|---|---|---|
| 17 | (CH₃)₃C— | 3,5-dimethylpiperidino | HCl | | 158–162 |
| 18 | CH₃CH₂C(CH₃)₂— | 2,6-dimethylmorpholino | | 137/0.15 | |
| 19 | CH₃CH₂C(CH₃)₂— | 3,5-dimethylpiperidino | — | 138–145/0.15 | |
| 20 | CH₃CH₂C(CH₃)₂— | 3-methylpiperidino | — | 135–140/0.25 | |
| 21 | C₆H₅—CH₂— | 2,6-dimethylmorpholino | — | 173–179/0.05 | |
| 22 | C₆H₅—CH₂— | 2,6-dimethylpiperidino | — | 175–183/0.02 | |
| 23 | C₆H₅— | 3,5-dimethylpiperidino | — | 170–177/0.05 | |
| 24 | (CH₃)₂CH—CH₂— | 2,6-dimethylmorpholino | — | 137–140/0.3 | |
| 25 | CH₃CH₂— | octahydroindol-1-yl | — | 118–125/0.3 | |
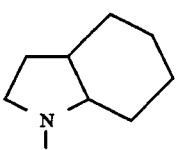

TABLE II-continued

| CMPD NO. | R | NR¹R² | SALT | b.p. (°C.)/mmHg | m.p. (°C.) |
|---|---|---|---|---|---|
| 26 | phenyl | 3,5-dimethylpiperidin-1-yl | — | 173–178/0.2 | |
| 27 | benzyl | 2,6-dimethylmorpholin-4-yl | HCl | | 140 |
| 28 | benzyl | 3,5-dimethylpiperidin-1-yl | HCl | | 143 |
| 29 | benzyl | morpholin-4-yl | — | 158–162/0.25 | |
| 30 | benzyl | piperidin-1-yl | — | 157–161/0.25 | |
| 31 | CH₃CH₂C(CH₃)₂CH₃ (tert-amyl) | 2,6-dimethylmorpholin-4-yl | HCl | | 138 |
| 32 | CH₃CH₂C(CH₃)₂CH₃ (tert-amyl) | 3,5-dimethylpiperidin-1-yl | HCl | | 170 |
| 33 | benzyl | 2-methylpiperidin-1-yl | — | 154–160/0.2 | |
| 34 | benzyl | 3-methylpiperidin-1-yl | — | 156–161/0.25 | |
| 35 | CH₃CH₂C(CH₃)₂CH₃ (tert-amyl) | decahydroisoquinolin-2-yl | — | 175–180/0.15 | |

TABLE II-continued

| CMPD NO. | R | NR¹R² | SALT | b.p. (°C.)/mmHg | m.p. (°C.) |
|---|---|---|---|---|---|
| 36 | (CH₃)₂CH—CH₂— | 3,5-dimethylpiperidin-1-yl | — | 133–136/0.3 | |
| 37 | (CH₃)₂CH—CH₂— | morpholin-4-yl | — | 103–107/0.05 | |
| 38 | (CH₃)₂CH—CH₂— | 2,6-dimethylpiperidin-1-yl | — | 138/0.3 | |
| 39 | (CH₃)₂CH—CH₂— | 3-methylpiperidin-1-yl | — | 108–113/0.1 | |
| 40 | (CH₃)₂CH—CH₂— | octahydroindol-1-yl | — | 128–136/0.1 | |
| 41 | (CH₃)₂CH—CH₂— | 2-methylpiperidin-1-yl | — | 118–125/0.15 | |
| 42 | (CH₃)₂CH—CH₂— | decahydroisoquinolin-2-yl | — | 155–163/0.3 | |
| 43 | (CH₃)₂CH—CH₂— | piperidin-1-yl | — | 125/0.5 | |
| 44 | (CH₃)₂CH—CH₂— | 2,6-dimethylmorpholin-4-yl | HCl | | 112 |
| 45 | (CH₃)₂CH—CH₂— | decahydroisoquinolin-2-yl | HCl | | 170 |
| 46 | C₆H₅—CH₂— | decahydroisoquinolin-2-yl | — | (See NMR Data) | |

TABLE II-continued
| CMPD NO. | R | NR¹R² | SALT | b.p. (°C.)/mmHg | m.p. (°C.) |
|---|---|---|---|---|---|
| 47 | 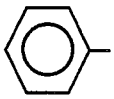 | 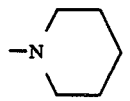 | — | 165/0.2 | |
| 48 | 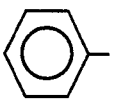 | 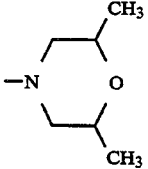 | — | 165–170/0.2 | |
| 49 | 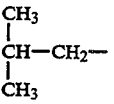 | 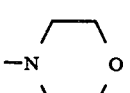 | HCl | | 165 |
| 50 | 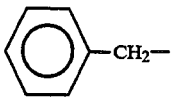 | 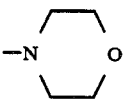 | HCl | | 145 |
| 51 | 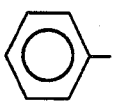 | 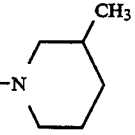 | — | 162–166/0.2 | |
| 52 | 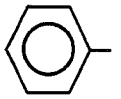 | 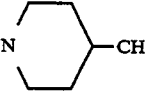 | — | 159–174/0.2 | |
| 53 | 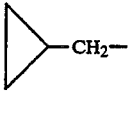 | 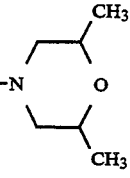 | — | 136–143/0.25 | |
| 54 | 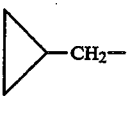 | 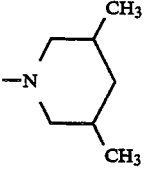 | — | 125–135/0.2 | |
| 55 | 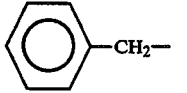 | 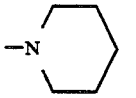 | HCl | | 150 |
| 56 | 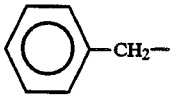 | 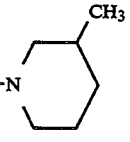 | HCl | | 130 |
| 57 | 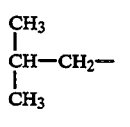 | 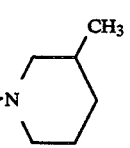 | HCl | | 124 |

TABLE II-continued

| CMPD NO. | R | NR¹R² | SALT | b.p. (°C.)/mmHg | m.p. (°C.) |
|---|---|---|---|---|---|
| 58 | CH₃CH₂— | 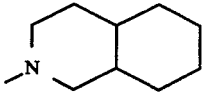 | — | 154–160/0.5 | |
| 59 | CH₃−CH−CH₂CH₂—<br>CH₃ | 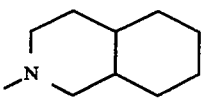 | — | 165–170/0.1 | |
| 60 | CH₃−CH−CH₂CH₂—<br>CH₃ | 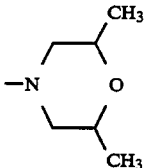 | — | 127–133/0.1 | |
| 61 | CH₃−C(CH₃)−CH₂CH₂<br>CH₃ | 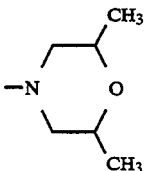 | — | 140–145/0.2 | |
| 62 | CH₃−C(CH₃)−CH₂CH₂<br>CH₃ | 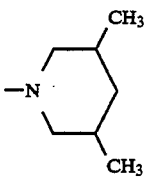 | — | 145–150/0.2 | |
| 63 | (CH₃)₃C— | 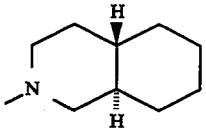 | — | 160–164/0.25 | |
| 64 | (CH₃)₃C— | 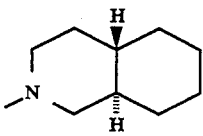 | HCl | | 188–190 |

NMR Data

The NMR data for Compound Number 46, noted above in Table II and as determined utilizing deuterated chloroform, are as follows: (CDCl₃) δ: 7.22 (5H, s), 6.55 (2H, s), 4.9 (2H, broad s), 4.05 (2H, s), 3.46 (2H, s), 2.76 (2H, s), 0.90–2.90 (16H, m)

Example 8

Preparation of Fungicidal Compositions

Each of Compound Nos. 1 through 64, summarized in Table II above, was dissolved either in acetone or in a solvent suitable for such compound. (0.3 g of each such compound in 10 ml of suitable solvent.) Thereafter, one or two drops of a commercially-available emulsifying agent, Triton X-100 [trademark] emulsifying agent, together with a sufficient amount of distilled water, were added to the resulting solution, to form an emulsion. The amount of water added was a function of the concentration of fungicidally-active ingredient, reported in milligrams per liter (mg/l), that was desired in the resulting emulsion composition.

Example 9

Control Of Powdery Mildew Fungus By Systemic Root Uptake

Emulsion compositions formed in accordance with the procedures of Example 8, including one of the Compound Nos. 1 through 64, were tested to evaluate effectiveness in either preventing or otherwise controlling powdery mildew disease of barley, caused by the fungus *Erysiphe graminis*, as well as powdery mildew disease of cucumber, caused by the fungus *Erysiphe cichoracearum*.

Such prevention or control capability was tested by utilizing the compounds of the present invention to control these diseases by systemic root uptake. In accordance with this purpose, a sufficient number of pots, each measuring 4×4×3.5 inches and containing either 10 plants of barley (Variety "Herta") or 10 plants of cucumber (Variety "Marketmore 70") were grown to ages of six days and ten days, respectively. Upon reaching these ages, emulsion compositions (45 ml.) of Compounds 1 to 64, formed in accordance with the procedure of Example 8, were added to each pot.

In particular, 45 ml of emulsion composition containing a respective one of the compounds tabulated in Table II were added to each such pot, in a manner so as to saturate the soil in each pot, without enduring significant loss of emulsion through drainage into the saucers below the pots. Each of the emulsion compositions contained the compounds of the present invention in a concentration of 250 milligrams of such compound per liter of water (mg/l). A number of pots containing the same barley and cucumber plants were left untreated as controls.

The barley and cucumber plants in all the pots, including those treated and those untreated, were inoculated with powdery mildew fungus 24 hours after emulsion-composition treatment with the compounds of the present invention.

Fungus inoculation was accomplished by tapping leaves of previously infected barley and cucumber plants, respectively, over the treated and untreated pots, to distribute spores of the fungus over the plants growing in such pots.

Six (6) days after inoculation, fungal disease control was evaluated on a 0 to 6 rating scale. A zero (0) rating was assigned when no disease was evidenced. A rating of six (6) was given for severe disease.

Intermediate ratings were assigned depending on the degree of disease. Percent control was computed by comparing the ratings of the treated and untreated plants.

The results of this test are reported in Table III wherein systemic control of powdery mildew disease in barley is reported under the heading titled "BMS 250." While systemic control of cucumber powdery mildew disease is reported in Table III under the heading titled "CMS 250."

Example 10

Control Of Powdery Mildew Fungus By Foliar Application

Eight plants of barley (Variety "Larker") were planted, as in Example 9, in pots sufficient in number to accommodate testing in duplicate or triplicate for each of the 64 compounds tabulated in Table II.

A duplicate number of pots, each containing eight plants, was utilized for control purposes.

Each of the 64 compounds was formulated into an emulsion composition, at a concentration of 1,000 milligrams of compound per liter of water (1,000 mg/l). Each such emulsion was then sprayed onto the foliage of the barley plants.

Unsprayed plants acted as controls. The number of pots which were unsprayed equalled the number sprayed.

After the foliage of the sprayed pots were dried, those pots containing the sprayed as well as the unsprayed plants were all placed in a greenhouse maintained at 21° C. All plants in these pots were next inoculated with barley powdery mildew fungus *Erysiphe graminis*.

Inoculation of this fungus was again accomplished by distributing spores of the fungus over the leaves of the plants to be tested from plants which had previously been infected with the disease.

Five (5) days following inoculation, the plants were evaluated and assigned a rating of "0 to 6" in accordance with the disease-rating criteria described in Example 9. Percentage control was computed in accordance with the description of Example 9. Results are summarized in Table III under the heading titled "BMP 1,000."

Similarly, pinto bean plants were prepared, treated and inoculated with the fungus *Erysiphe polygoni*, and the results are summarized in Table III under the heading titled "PMP 1,000."

TABLE III

| COMPOUND NUMBER | BMS 250 | CMS 250 | BMP 1000 | PMP 1000 |
|---|---|---|---|---|
| 1 | 60 | 0 | 100 | — |
| 2 | 0 | 0 | 0 | 0 |
| 3 | 0 | 0 | 0 | 0 |
| 4 | 0 | 0 | 20 | 0 |
| 5 | 65 | 0 | 90 | 50 |
| 6 | 0 | 0 | 20 | 0 |
| 7 | 90 | 0 | 90 | 0 |
| 8 | 40 | 0 | 0 | 0 |
| 9 | 90 | 80 | 0 | 0 |
| 10 | 00 | 80 | 0 | 0 |
| 11 | 0 | 0 | 0 | 0 |
| 12 | 0 | 0 | 0 | 0 |
| 13 | 100 | 80 | 20 | 50 |
| 14 | 90 | 0 | 20 | 30 |
| 15 | 0 | 0 | 100 | 75 |
| 16 | 0 | 0 | 100 | 80 |
| 17 | 100 | 100 | 75 | 100 |
| 18 | 0 | 15 | 35 | 70 |
| 19 | 100 | 0 | 80 | 95 |
| 20 | 100 | 0 | — | — |
| 21 | 0 | 0 | 100 | 0 |
| 22 | 35 | 0 | 80 | 0 |
| 23 | 90 | 0 | — | 80 |
| 24 | 0 | 0 | 60 | 0 |
| 25 | 0 | 0 | 60 | 0 |
| 26 | 0 | 0 | 0 | 0 |
| 27 | 0 | 0 | 60 | 0 |
| 28 | 0 | 0 | — | 75 |
| 29 | 0 | 0 | 0 | 0 |
| 30 | 0 | 0 | 0 | 0 |
| 31 | 0 | 0 | 0 | 0 |
| 32 | 0 | 0 | 95 | 95 |
| 33 | 0 | 0 | 20 | 50 |
| 34 | 0 | 0 | 20 | 0 |
| 35 | 40 | 80 | 0 | 100 |
| 36 | 40 | 80 | 0 | 0 |
| 37 | 40 | 20 | 95 | 95 |
| 38 | 0 | 100 | 95 | 95 |
| 39 | 60 | 46 | 90 | 90 |
| 40 | 40 | 60 | 100 | 100 |
| 41 | 0 | 0 | 0 | 60 |
| 42 | 60 | 0 | — | 100 |
| 43 | 60 | 0 | 0 | 90 |
| 44 | 20 | 0 | 0 | 0 |
| 45 | 0 | 0 | 20 | 100 |
| 46 | — | — | — | 95 |
| 47 | 0 | 0 | — | 20 |
| 48 | 0 | 0 | — | 95 |
| 49 | 25 | 0 | 0 | 0 |
| 50 | 50 | 0 | 0 | 95 |
| 51 | 0 | 0 | — | — |
| 52 | 50 | 0 | — | 75 |
| 53 | 0 | 0 | — | 45 |
| 54 | 75 | 90 | — | 95 |
| 55 | 60 | — | — | 25 |
| 56 | 60 | 0 | — | 100 |
| 57 | 70 | 20 | — | 100 |
| 58 | 95 | 40 | — | 80 |
| 59 | 0 | 40 | — | 100 |
| 60 | 0 | 0 | 0 | 90 |
| 61 | 40 | 0 | 60 | 95 |
| 62 | 60 | 0 | 20 | 100 |
| 63 | 100 | 100 | — | — |

TABLE III-continued

| COMPOUND NUMBER | BMS 250 | CMS 250 | BMP 1000 | PMP 1000 |
|---|---|---|---|---|
| 64 | 100 | 100 | 100 | 100 |

Example 11

Control Of Rice Blast Disease By Foliar Treatment

Five rice plants (Variety "Bellemont") were planted in pots sufficient in number to accommodate the following criteria.

The number of pots utilized equalled two times the number of compounds of the present invention in Table II plus a control for each replication of the test. The non-control pots were sprayed with emulsion compositions, formed in accordance with the procedure of Example 8, wherein each compound was provided at a concentration of 1,000 mg/l. This spraying occurred 3 to 4 weeks after planting of the plants in the pots. The controls remained unsprayed.

The sprayed and unsprayed plants, five to a pot, were inoculated with spores of the rice blast fungus *Pyricularia oryzae*. Inoculation was accomplished by preparing inoculum containing 20,000 to 30,000 spores per milliliter. Such inoculum was then sprayed onto those plants to which one or two drops of ethoxylated sorbitan monolaurate surfactant had been earlier applied, for purposes of ensuring proper wetting of the inoculum onto the plant foliage.

The inoculated plants in the control and non-control pots were incubated in a control chamber, at a relative humidity of 99% and at a temperature of 21° C., for about 24 hours to allow infection to occur. The plants, after 24 hours in the control chamber, were next transferred to a greenhouse for six days to permit disease development to occur. Disease was manifested by blast lesions on the leaves.

Disease control was calculated by one of two methods. In one method the number of lesions was counted, if infection was moderate. Alternatively, in the case of severe infection, disease was evaluated by the "0 to 6" rating system discussed in Example 9.

The rating system that was used to determine disease-treating value of any particular compound was also used to evaluate its control.

The results of this test are summarized and tabulated in Table IV under the heading titled "RCB 1,000."

Example 12

Control Of Bean Rust Fungus By Eradicant Action

Two varieties of pinto bean plant *Phaseolus vulgaris* were planted in pots sufficient in number to accommodate the following criteria.

When the plants were seven days old, at the primary leaf stage of growth, they were sprayed with an aqueous suspension containing about 20,000 spores of the bean rust fungus *Uromyces phaseoli* per milliliter of suspensing water.

All pots containing inoculated plants were then incubated in a controlled-environment chamber, maintained at 99% relative humidity and a temperature of 21° C., for 24 hours to allow infection to develop.

Thereafter the plants were removed from the incubator and allowed to dry. Two days following inoculation, the infected plants were sprayed with compositions containing the compounds tabulated in Table II.

Such compositions were prepared in accordance with the procedure of Example 11, to provide a concentration of 1,000 mg/l.

An equal number of infected plants were not sprayed, so that they could act as controls. All sprayed and unsprayed plants were placed for five (5) days in a greenhouse maintained at a temperature of 21° C., to assess for disease. The sprayed and control plants were assessed for disease using the "0 to 6" rating system described in Example 9.

Results, expressed as percent reduction of disease, are summarized and tabulated in Table IV under the heading titled "BRE 1,000."

Example 13

Control Of Peanut Cercospora Leafspot By Foliar Treatment

Four Virginia-runner peanut plants were grown in pots sufficient in number to accommodate the following criteria.

Enough pots were used so that each of the compounds listed in Table II, prepared as an emulsion in accordance with the procedures of Example 8, could be evaluated by spraying each such emulsion onto the four (4) Virginia-runner peanut plants of each pot containing these plants.

An equal number of pots, containing plants that were not sprayed, were used as controls. Spraying occurred when the peanut plants were four weeks old. The concentration of emulsion used to spray the plants was 900 mg/l.

All plants, sprayed and unsprayed, were thereafter inoculated with spores of the peanut leafspot fungus *Cercospora arachidicola*.

The inoculum contained 20,000 to 30,000 spores per milliliter. Such inoculum, treated with one or two drops of ethoxylated sorbitan monolaurate to aid in wetting the leaves, was thereafter sprayed onto the leaves of the peanut plants.

Pots containing inoculated peanut plants were incubated for thirty six (36) hours in a control chamber maintained at a temperature of 24° C., to develop infection. Thereafter, the plants were placed in a greenhouse for twenty-one (21) days, to allow disease development to occur.

After twenty-one (21) days in the greenhouse, all the plants were taken out and evaluated using the "0 to 6" disease-rating system.

Percent control was computed and the results are summarized and presented in Table IV under the heading titled "PNT 900."

Example 14

Control Of Barley Blast By Foliar Treatment

Ten (10) plants of six (6) day-old barley (Variety "Herta") were obtained and planted in pots sufficient in number to accommodate the following criteria. A sufficient number of pots were obtained and sprayed with emulsion compositions formulated in accordance with the procedure of Example 8, so that there was a pot for each compound set forth in Table II.

An equal number of pots, containing plants that were not sprayed, were used as controls.

All plants, sprayed and unsprayed, were thereafter inoculated with spores of the rice blast fungus *Pyricularia oryzae*. Inoculation was as set forth in Example 11, which employed the same fungus.

All inoculated plants were thereafter placed in a greenhouse, maintained at a temperature of 21° C., for five (5) days. During that time, the plants were evaluated using the "0 to 6" disease-rating system.

Percent control was computed and the results are summarized and presented in Table IV under the heading titled "BBL 1,000."

TABLE IV

| COMPOUND NUMBER | RCB 1000 | BRE 1000 | PNT 900 | BBL 1000 |
|---|---|---|---|---|
| 1 | 0 | — | — | 1000 |
| 2 | — | 0 | — | 0 |
| 3 | — | 95 | 0 | 85 |
| 4 | — | 65 | — | 65 |
| 5 | — | 100 | 60 | 90 |
| 6 | — | 95 | 0 | 15 |
| 7 | — | 33 | 50 | 0 |
| 8 | 0 | 0 | — | 0 |
| 9 | — | 0 | — | 15 |
| 10 | — | 75 | 0 | 15 |
| 11 | — | 85 | 0 | 0 |
| 12 | — | 0 | — | 0 |
| 13 | — | 100 | — | 65 |
| 14 | — | 60 | — | 0 |
| 15 | 88 | 100 | — | 85 |
| 16 | — | 100 | — | 20 |
| 17 | — | 100 | — | 0 |
| 18 | — | 100 | — | 75 |
| 19 | — | 100 | 8 | 50 |
| 20 | — | — | 0 | — |
| 21 | 0 | 0 | — | 85 |
| 22 | 0 | 0 | — | 85 |
| 23 | — | 100 | 0 | — |
| 24 | — | 0 | — | 35 |
| 25 | — | 0 | — | 0 |
| 26 | — | 30 | 0 | 65 |
| 27 | — | 0 | — | 15 |
| 28 | — | 95 | — | — |
| 29 | — | 35 | — | 50 |
| 30 | — | 60 | — | — |
| 31 | 0 | 75 | — | 100 |
| 32 | — | 100 | — | 35 |
| 33 | 0 | 95 | — | 85 |
| 34 | — | 95 | — | 0 |
| 35 | — | 100 | — | 0 |
| 36 | — | 0 | — | 0 |
| 37 | — | 100 | — | — |
| 38 | — | 100 | — | — |
| 39 | — | 100 | — | — |
| 40 | — | 100 | — | 0 |
| 41 | — | 95 | — | 0 |
| 42 | — | 100 | — | — |
| 43 | — | 100 | — | 0 |
| 44 | — | 30 | — | 0 |
| 45 | — | 100 | — | 0 |
| 46 | — | 100 | — | — |
| 47 | — | 50 | — | — |
| 48 | — | 100 | 0 | — |
| 49 | — | 0 | 0 | 0 |
| 50 | — | 95 | — | 0 |
| 51 | — | 100 | 0 | — |
| 52 | — | 100 | — | — |
| 53 | — | 90 | 10 | — |
| 54 | — | 100 | 15 | — |
| 55 | — | 95 | — | — |
| 56 | — | 100 | — | — |
| 57 | — | 100 | 0 | — |
| 58 | — | 95 | 20 | — |
| 59 | — | 100 | — | — |
| 60 | — | 100 | — | 40 |
| 61 | — | 100 | 0 | 55 |
| 62 | — | 100 | 50 | 10 |
| 63 | — | — | — | — |
| 64 | — | 100 | — | 100 |

Example 15

Control Of Barley Spot Blotch By Foliar Treatment

Ten (10) plants of six (6) day-old Barley (Variety "Robust") were obtained and planted in pots sufficient in number to accommodate the following criteria. A sufficient number of pots were obtained and sprayed with emulsion compositions formulated in accordance with the procedure of Example 10, so that there was a pot for each compound set forth in Table II.

An equal number of pots, containing plants that were not sprayed, were used as controls.

All plants, sprayed and unsprayed, were thereafter inoculated with spores of the blotch fungus *Helrninthosporium sativum*. The method of inoculation was as set forth in Examples 11 and 12.

All inoculated plants were thereafter placed in a greenhouse, maintained at a temperature of 21° C., for five (5) days. After that time, the plants were evaluated using the "0 to 6"disease-rating system.

Percent control was computed and the results are summarized and presented in Table V under the heading titled "HSAT 1,000."

Example 16

Control Of Seven Fungus Species

Each of Compound Nos. 1 to 64 listed in Table II were solubilized in acetone at a concentration of 500 mg/l, producing 64 test solutions.

A sufficient number of filter-paper discs, each 11 mm in diameter, and agar plates were obtained to accommodate the following criteria.

A separate filter-paper disc was dipped into one of each of the sixty-four (64) different test solutions. The filter-paper discs were next air dried, to drive off the acetone solvent.

An equal number of discs, untreated, served as controls.

Each of the discs, treated and untreated, was then placed on an agar plate.

Thereafter, one of seven fungus species, in the form of a culture plug, was added to the center of each treated and untreated paper disc.

Six (6) of the seven (7) fungus species thus tested included:

*Alternaria solani* ("ALT"), *Botrytis cinerea* ("BOT"), *Fusarium oxysporum* ("FUS"), *Phytophthora infestans* ("PHY"), *Sclerotinia sclerotiorum* ("SCM") and *Sclerotium rolfsii* ("SCO").

The plates were incubated at 29° C. in an oven.

Percent growth inhibition by the compounds of the present invention of the six (6) identified-above fungus species was evaluated, after incubation, by measuring the radius from the center of the fungus colony of the treated discs compared to the radius from the center of the fungus colony of the untreated discs. That is, inhibition effectuated by each of the compounds was determined as a function of the percent difference between the radii of the treated and untreated discs.

Some of the results of these tests appear in Table V under the headings titled "ALT 500," "BOT 500" and "FUS 500," While the remainder of the results of these tests appear in Table VI under the headings titled "PHY 500," "SCM 500" and "SCO 500."

A separate test was utilized to determine the control of the seventh fungus species *Cercospora arachidicola* ("CER").

In this seventh test, two drops of the above-identified fungus were added as a spore suspension (about 20,000 spores per milliliter) to the chemically treated discs, rather than as a mycelial culture plug. Scoring of the effectiveness of the compounds in controlling the *Cercospora arachidicola* fungus was determined with control based on the following scoring criteria: 100 represented complete inhibition of germination and growth of the fungus; 80 represented nearly complete inhibition but some growth of the fungus; 50 represented partial inhibition of growth or early complete inhibition with later growth; 20 indicated some, but not significant, inhibition of growth; and 0 indicated complete growth of the fungus without any inhibition.

The results representing the effectiveness of the compounds of Table II against *Cercospora arachidicola* are summarized and included in Table VI under the heading titled "CER 500."

TABLE V

| COMPOUND NUMBER | HSAT 1000 | ALT 500 | BOT 500 | FUS 500 |
|---|---|---|---|---|
| 1 | 100 | 85 | 45 | 40 |
| 2 | 80 | 55 | 25 | 15 |
| 3 | 90 | 95 | 100 | 30 |
| 4 | 85 | 75 | 71 | 30 |
| 5 | 100 | 100 | 100 | 93 |
| 6 | 95 | 25 | 100 | 40 |
| 7 | 94 | 92 | 100 | 45 |
| 8 | 100 | 45 | 94 | 10 |
| 9 | 100 | 100 | 96 | 25 |
| 10 | 100 | 100 | 100 | 85 |
| 11 | 100 | 80 | 100 | 5 |
| 12 | 100 | 60 | 100 | 50 |
| 13 | 100 | 60 | 100 | 20 |
| 14 | 97 | 45 | 100 | 30 |
| 15 | 70 | 25 | 75 | 0 |
| 16 | 100 | 50 | 100 | 0 |
| 17 | 100 | 50 | 100 | 0 |
| 18 | 84 | 45 | 100 | — |
| 19 | 85 | 100 | 100 | 30 |
| 20 | 100 | 96 | 100 | 60 |
| 21 | 55 | 75 | 100 | 55 |
| 22 | 95 | 85 | 35 | 80 |
| 23 | 100 | 100 | 100 | 90 |
| 24 | 90 | 55 | 90 | 40 |
| 25 | 85 | 85 | 80 | 25 |
| 26 | 86 | 80 | 100 | 30 |
| 27 | 93 | 55 | 70 | 5 |
| 28 | 90 | 99 | 45 | 35 |
| 29 | 60 | 75 | 100 | 45 |
| 30 | 70 | 80 | 77 | 55 |
| 31 | 80 | 75 | 60 | 5 |
| 32 | 80 | 100 | 70 | 10 |
| 33 | 86 | 85 | 50 | 55 |
| 34 | 70 | 65 | 40 | 60 |
| 35 | 88 | 100 | 93 | 40 |
| 36 | 80 | 60 | 100 | 10 |
| 37 | 75 | 45 | 80 | 0 |
| 38 | 65 | 75 | 70 | 25 |
| 39 | 90 | 65 | 100 | 40 |
| 40 | 94 | 95 | 65 | 50 |
| 41 | 85 | 70 | 100 | 40 |
| 42 | 90 | 100 | 50 | 40 |
| 43 | 75 | 65 | 45 | 20 |
| 44 | 70 | 40 | 100 | 20 |
| 45 | 85 | 100 | 75 | 45 |
| 46 | 75 | 100 | 25 | 45 |
| 47 | 100 | 75 | 30 | 30 |
| 48 | 75 | 50 | 85 | 25 |
| 49 | 75 | 45 | 100 | 15 |
| 50 | 70 | 85 | 80 | 20 |
| 51 | 100 | 70 | 75 | 20 |
| 52 | 86 | 60 | 80 | 25 |
| 53 | 75 | 40 | 100 | 15 |
| 54 | 100 | 50 | 100 | 5 |
| 55 | 70 | 90 | 25 | 35 |
| 56 | 85 | 93 | 90 | 50 |
| 57 | 80 | 70 | 100 | 20 |
| 58 | 75 | 85 | 65 | 25 |
| 59 | 100 | 35 | 100 | 20 |
| 60 | 60 | 70 | 100 | 5 |
| 61 | 100 | 75 | 100 | 15 |
| 62 | 88 | 80 | 100 | 15 |
| 63 | 100 | 100 | 100 | 40 |
| 64 | 100 | 100 | 100 | 5 |

TABLE VI

| COMPOUND NUMBER | PHY 500 | SCM 500 | SCO 500 | CER 500 |
|---|---|---|---|---|
| 1 | 0 | 0 | 0 | 100 |
| 2 | 0 | 0 | 0 | 70 |
| 3 | 65 | 0 | 65 | 100 |
| 4 | 45 | 0 | 0 | 100 |
| 5 | 100 | 0 | 100 | 100 |
| 6 | 65 | 0 | 80 | 100 |
| 7 | 38 | 55 | 100 | 100 |
| 8 | 50 | 0 | 0 | 100 |
| 9 | 60 | 10 | 15 | 100 |
| 10 | 90 | 35 | 60 | 00 |
| 11 | 65 | 10 | 25 | 100 |
| 12 | 70 | 20 | 20 | 100 |
| 13 | 70 | 25 | 100 | 70 |
| 14 | 80 | 25 | 70 | 80 |
| 15 | 50 | 0 | 55 | 80 |
| 16 | 40 | 0 | 76 | 70 |
| 17 | 40 | 0 | 100 | 70 |
| 18 | 80 | 91 | 100 | 100 |
| 19 | 85 | 45 | — | 100 |
| 20 | 80 | 55 | — | 100 |
| 21 | 75 | 0 | — | 70 |
| 22 | 30 | 0 | — | 100 |
| 23 | 75 | 30 | — | 100 |
| 24 | 30 | 50 | — | 70 |
| 25 | 10 | 15 | 100 | 85 |
| 26 | 40 | 10 | 100 | 100 |
| 27 | 91 | 40 | — | 0 |
| 28 | — | 35 | 100 | 0 |
| 29 | 35 | 25 | — | 70 |
| 30 | 5 | 0 | 100 | 70 |
| 31 | 30 | 60 | — | 0 |
| 32 | 0 | 45 | — | 0 |
| 33 | 0 | 10 | 100 | 70 |
| 34 | 50 | 20 | — | 0 |
| 35 | 100 | 45 | 100 | 70 |
| 36 | 100 | 35 | 100 | 100 |
| 37 | 5 | 25 | 100 | 70 |
| 38 | 5 | 25 | 100 | 70 |
| 39 | 20 | 20 | 100 | 70 |
| 40 | 30 | 20 | 100 | 80 |
| 41 | 5 | 25 | 100 | 70 |
| 42 | 30 | 20 | 100 | 70 |
| 43 | 5 | 0 | 100 | 70 |
| 44 | 15 | 30 | 100 | 70 |
| 45 | 30 | 40 | 100 | 70 |
| 46 | 50 | 5 | 35 | 70 |
| 47 | 10 | 0 | — | 70 |
| 48 | 55 | 35 | 76 | 70 |
| 49 | 5 | 25 | — | 70 |
| 50 | 50 | 0 | 37 | 70 |
| 51 | 20 | 40 | 68 | 100 |
| 52 | 15 | 0 | 100 | 70 |
| 53 | 60 | 25 | 100 | 100 |
| 54 | 75 | 0 | 100 | 100 |
| 55 | 20 | 0 | 62 | 70 |
| 56 | 65 | 15 | 100 | 100 |
| 57 | 15 | 25 | 100 | 100 |
| 58 | 25 | 0 | 100 | 100 |
| 59 | 70 | 50 | — | 0 |
| 60 | 45 | 80 | — | 0 |
| 61 | 85 | 65 | 100 | 100 |
| 62 | 50 | 45 | 100 | 100 |
| 63 | 100 | 65 | 100 | 0 |
| 64 | 100 | 30 | 100 | 0 |

What has been described herein is a novel class of thiophene substituted cycloamines which we have found to be useful as fungicides. While our invention has been discussed and described with reference to

We claim:
1. A compound having the structural formula

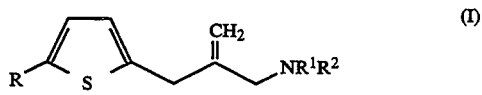

where R is $C_1$–$C_8$ alkyl, $C_3$–$C_6$ cycloalkyl, phenyl or substituted phenyl; N, $R^1$ and $R^2$ form a monocyclic or bicyclic nitrogen heterocycle which is at least partially saturated and which may contain oxygen or sulfur or be substituted with lower alkyl; and physiologically acceptable salts thereof.

2. A compound in accordance with claim 1 where R is $C_4$ to $C_8$ alkyl, phenyl, or phenylmethyl; and N, $R^1$ and $R^2$ together form a monocyclic or bicyclic nitrogen heterocycle that is least partially saturated.

3. A compound in accordance with claim 1 where R is 1,1-dimethylethyl, 1,1-dimethylpropyl, 5-phenyl methyl, 3-methylbutyl, or 3,3-dimethylbutyl; and N, $R^1$ and $R^2$ form partially saturated isoquinolinyl-, piperidinyl-, morpholinyl-, or partially saturated quinolinyl- which may be substituted with $C_1$–$C_2$ alkyl and physiologically acceptable salts thereof.

4. A composition comprising the compound of claim 1 and a suitable carrier therefor.

5. A method for controlling phytopathogenetic fungi comprising applying a fungicidally effective amount of the compound of claim 1 to the locus under attack by said fungi.

6. A method for controlling phytopathogenetic fungi comprising applying a fungicidally effective amount of the compound of claim 1 to the foliage of the plant to be protected from said fungi.

7. A method in accordance with claim 6 wherein said compound is applied to said foliage in the concentration in the range of between about 10 and about 1000 milligrams per liter.

8. A method for controlling phytopathogenetic fungi comprising applying a fungicidally effective amount of the compound of claim 1 to the soil in which the soil to be protected from phytopathogenic fungi is grown.

9. A method in accordance with claim 8 wherein said compound is applied to the soil in a concentration in the range of between about 0.125 and about 10 kilograms per hectare.

10. A method for controlling phytopathogenetic fungi comprising coating seeds of the plant to be protected with a fungicidally effective amount of the compound of claim 1.

11. A method in accordance with claim 10 wherein said coating is applied in a concentration in the range of between about 5 and about 150 grams of compound per 100 kilograms of seed.

* * * * *